United States Patent
Hübsch et al.

(10) Patent No.: US 6,700,017 B1
(45) Date of Patent: Mar. 2, 2004

(54) METHODS FOR PRODUCING 2-(2-HYDROXYPHENYL)-2-(ALKOXYIMINO)-N-METHYLACETAMIDE DERIVATIVES

(75) Inventors: Walter Hübsch, Wuppertal (DE);
Bernd Gallenkamp, Wuppertal (DE);
Herbert Gayer, Monheim (DE);
Lubbertus Mulder, Hagen (DE);
Thorsten Müh, Leverkusen (DE);
Reinhard Lantzsch, Wuppertal (DE);
Holger Weintritt, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/130,810

(22) PCT Filed: Nov. 14, 2000

(86) PCT No.: PCT/EP00/11225

§ 371 (c)(1),
(2), (4) Date: May 20, 2002

(87) PCT Pub. No.: WO01/38294

PCT Pub. Date: May 31, 2001

(30) Foreign Application Priority Data

Nov. 26, 1999 (DE) .......................... 199 56 920

(51) Int. Cl.$^7$ ............................................ C07C 233/05
(52) U.S. Cl. ............................ 564/164; 564/169
(58) Field of Search ................................ 564/164, 169

(56) References Cited

U.S. PATENT DOCUMENTS

| | | | |
|---|---|---|---|
| 5,185,342 A | 2/1993 | Hayase et al. | 514/274 |
| 5,371,222 A | 12/1994 | Hayase et al. | 544/316 |
| 5,371,223 A | 12/1994 | Hayase et al. | 544/316 |
| 5,401,877 A | 3/1995 | Hayase et al. | 564/147 |
| 5,534,550 A | 7/1996 | Gerdes et al. | 514/620 |
| 5,548,078 A | 8/1996 | Hayase et al. | 544/298 |
| 5,693,859 A | * 12/1997 | Takase et al. | 564/169 |
| 5,723,471 A | 3/1998 | De Fraine | 514/274 |
| 5,734,062 A | 3/1998 | Lee et al. | 548/429 |

FOREIGN PATENT DOCUMENTS

| | | |
|---|---|---|
| EP | 0 398 692 | 11/1990 |
| EP | 0 605 392 | 7/1994 |
| EP | 0 629 609 | 12/1994 |
| WO | 5/24396 | 9/1995 |

OTHER PUBLICATIONS

H. Metzer, Houben–Weyl, Methoden der org. Chemie, vol. X/4 (month unavailable) 1968 pp. 217–223, "Unwandlung von Oximen".

J. Chem. Soc., Chem. Commun (month unavailable) 1972, (11), p. 668, Toshio Inque, Yasuo Shigemitsu, and Yoshinobu Odaira, A New Photo–Fries Reaarangement of Methyl Aryl Oxalates.

K. Fries und W. Pfaffendorf, Chem. Ber. 45,(month unavailable) 1912, pp. 154–162, "Cumarandion das Sauerstoff–Isologe des Isatins".

Willy. Logemann, Giancarlo Cavagna und Gianpaolo Tosoline, Chem. Ber. 96 (month unavailable) 1963, p. 2248–2250, "Notiz über die Oxydation von o–Hydroxy–acetophenon mit Selendioxyd".

Glen A. Russell, Charles L. Myers, Paolo Bruni, Franz A. Neugebauer and Ronald Blankespoor J. Am. Chem. Soc. 92 (month unavailable) 1970, p. 2762–2769, Semidiones. X Semidione Radical Anions Derived from Indan–2,3–dione, Coumaran–2,3–dione, Thianaphthalenequinone, Isatin, and N–Hydroxyisatin. Nitroxide Radicals Dervied from Isatin, Dioxindole, Oxindole, and Other Indole Derivatives.

* cited by examiner

Primary Examiner—Shailendra Kumar
(74) Attorney, Agent, or Firm—Richard E. L. Henderson

(57) ABSTRACT

The present invention provides processes for preparing 2-(2-hydroxyphenyl)-2-(alkoxyimino)-N-methylacetamides, to intermediates for this preparation, and to processes for preparing those intermediates.

1 Claim, No Drawings

METHODS FOR PRODUCING 2-(2-HYDROXYPHENYL)-2-(ALKOXYIMINO)-N-METHYLACETAMIDE DERIVATIVES

This application is a 371 of PCT/EP00/11225, filed Nov. 14, 2000.

FIELD OF THE INVENTION

The present application relates to a plurality of novel processes for preparing 2-(2-hydroxyphenyl)-2-(alkoxyimino)-N-methylacetamide derivatives, to novel intermediates for their preparation, and to processes for preparing these intermediates.

BACKGROUND OF THE INVENTION

It is already known that 2-(2-hydroxyphenyl)-2-(methoxyimino)-N-methylacetamide (C) is obtained when methyl 2-(2-hydroxyphenyl)-2-(methoxyimino)-acetate (A) or 1-benzofuran-2,3-dione 3-(O-methyl oxime) (B) is reacted with methylamine (compare, for example, EP-A 398692 or WO 95-24396):

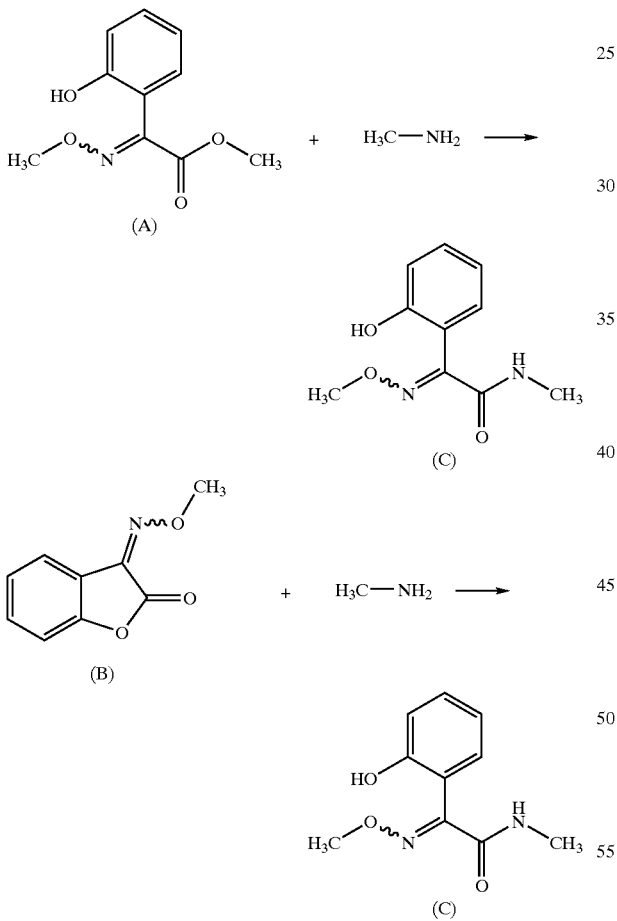

These processes have the disadvantage that the starting materials are difficult to obtain.

DETAILED DESCRIPTION OF THE INVENTION

It has now been found that 2-(2-hydroxyphenyl)-2-(alkoxyimino)-N-methylacetamide derivatives of the general formula (I)

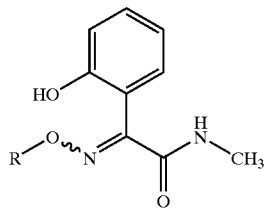

in which

R represents substituted or unsubstituted alkyl, are obtained when a) 2-(2-hydroxyphenyl)-2-(hydroxyimino)-N-methylacetamide of the formula (II)

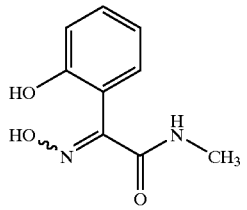

is reacted with alkylating agents of the formula (III)

R—X       (III)

in which

R is as defined above, and

X represents halogen, —O—CO—O—R, —O—SO$_2$—R$^1$ or —O—SO$_2$—O—R, where R is as defined above and R$^1$ represents alkyl or optionally alkyl-substituted phenyl, if appropriate in the presence of a diluent and if appropriate in the presence of an acid acceptor, if appropriate in the presence of a phase-transfer catalyst, or when b) 2-(2-hydroxyphenyl)-2-(methylimino)-N-methylacetamide of the formula (IV)

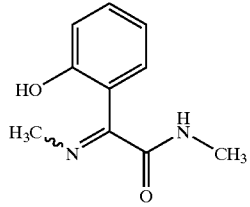

is reacted with alkoxyamines of the formula (V)

R—O—NH$_2$       (V)

in which

R is as defined above, or an acid addition complex thereof, if appropriate in the presence of a diluent and if appropriate in the presence of a buffer medium, or when c) 2-(2-hydroxyphenyl)-2-(oxo)-N-methylacetamide of the formula (VI)

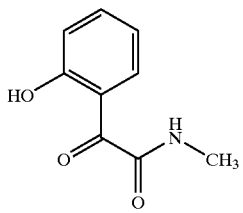

(VI)

is reacted with alkoxyamines of the formula (V)

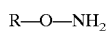

R—O—NH$_2$ (V)

in which
R is as defined above,
or an acid addition complex thereof,
if appropriate in the presence of a diluent and if appropriate in the presence of a buffer medium.

In the definition of R, the saturated hydrocarbon chains, such as alkyl, are in each case straight-chain or branched. In particular, alkyl represents $C_1$–$C_4$-alkyl, preferably methyl, ethyl, n- or i-propyl, n-, s- or i-butyl, n-pentyl or i-pentyl, in particular methyl, ethyl or n-propyl.

The preferred substituent for alkyl is halogen.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Suitable substituents for aryl are alkyl or halogen.

R represents in particular methyl, ethyl, fluoromethyl and difluoromethyl.

R particularly preferably represents methyl.

$R^1$ particularly preferably represents methyl or tolyl.

The abovementioned general or preferred radical definitions apply both to the end products of the formula (I) and, correspondingly, to the starting materials or intermediates required in each case for the preparation.

The particular radical definitions given for these radicals in the respective combinations or preferred combinations of radicals are, independently of the particular combination of radicals given, also replaced as desired by radical definitions of other preferred ranges.

If appropriate, the compounds according to the invention can be present as mixtures of different possible isomeric forms, in particular stereoisomers, such as, for example, E and Z. What is claimed are both the E and the Z isomers, and any desired mixtures of these isomers.

It is extremely surprising that the alkylation in the process a) according to the invention occurs selectively in high yield at the oxygen atom of the oxime group. In general, in the alkylation of oximes, mixtures of the O- and N-alkylation products are formed. A selective O-alkylation can otherwise only be realized with silver salts which are expensive or difficult to prepare (cf. H. Metzger in Houben-Weyl, Methoden der org. Chemie, Volume X/4, page 217 ff., 1968).

The process a) according to the invention has a number of advantages. Thus, 2-(2-hydroxyphenyl)-2-(alkoxyimino)-N-methylacetamide derivatives of the formula (I) can be obtained in high yields and purities from easily obtainable starting materials, under conditions which do not cause any technical problems at all.

It is extremely surprising that the selective exchange of the imino group in the process b) according to the invention occurs without any side reactions and under very simple conditions.

The process b) according to the invention has a number of advantages. Thus, 2-(2-hydroxyphenyl)-2-(alkoxyimino)-N-methylacetamide derivatives of the formula (I) can be obtained in high yields and purities from easily obtainable starting materials, under conditions which do not cause any technical problems at all.

It is extremely surprising that, in the process c) according to the invention, the derivatives of the formula (I) are obtained in high yields and high purity.

The process c) according to the invention has a number of advantages. Thus, 2-(2-hydroxyphenyl)-2-(alkoxyimino)-N-methylacetamide derivatives of the formula (I) can be obtained in high yields and purities from easily obtainable starting materials, under conditions which do not cause any technical problems at all.

The 2-(2-hydroxyphenyl)-2-(hydroxyimino)-N-methylacetamide of the formula (II) required as starting material for carrying out the process a) according to the invention has hitherto not been disclosed and, as novel chemical compound, also forms part of the subject-matter of the present application.

2-(2-Hydroxyphenyl)-2-(hydroxyimino)-N-methylacetamide of the formula (II) is obtained when d) 2-(2-hydroxyphenyl)-2-(methylimino)-N-methylacetamide of the formula (I)

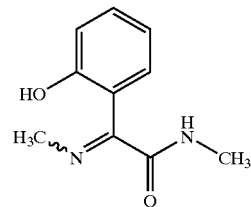

(IV)

is reacted with hydroxylamine or an acid addition complex thereof,
if appropriate in the presence of a diluent and if appropriate in the presence of a buffer medium, or when e) 2-(2-hydroxyphenyl)-2-oxo-N-methylacetamide of the formula (VI)

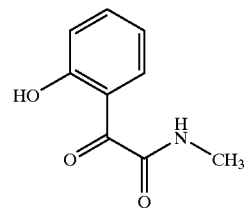

(VI)

is reacted with hydroxylamine or an acid addition complex thereof,
if appropriate in the presence of a diluent and if appropriate in the presence of a buffer medium.

It is extremely surprising that the selective exchange of the imino group by the process d) according to the invention proceeds under simple and mild conditions and without any side reactions.

The process d) according to the invention has a number of advantages. Thus, 2-(2-hydroxyphenyl)-2-(hydroxyimino)-

N-methylacetamide of the formula (II) can be obtained in high yields and purities from easily obtainable starting materials, under conditions which do not cause any technical problems at all.

It is extremely surprising that the reaction with hydroxylamine by the process e) according to the invention takes place selectively at the keto group.

The process e) according to the invention has a number of advantages. Thus, 2-(2-hydroxyphenyl)-2-(hydroxyimino)-N-methylacetamide of the formula (II) can be obtained in high yields and purities from easily obtainable starting materials, under conditions which do not cause any technical problems at all.

The 2-(2-hydroxyphenyl)-2-(methylimino)-N-methylacetamide of the formula (IV) required as starting material for carrying out the processes b) and d) according to the invention has hitherto not been disclosed and, as novel chemical compound, also forms part of the subject-matter of the present application.

2-(2-Hydroxyphenyl)-2-(methylimino)-N-methylacetamide of the formula (IV)

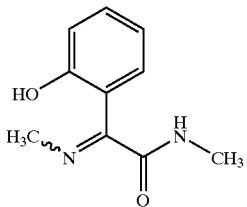

(IV)

is obtained when f) an alkyl (2-hydroxyphenyl)-oxoacetate of the general formula (VII)

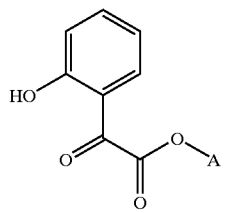

(VII)

in which
A represents alkyl or optionally substituted aryl,
is reacted with methylamine, if appropriate in the presence of a diluent, or when g) 1-benzofuran-2,3-dione of the formula (VIII)

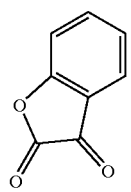

(VIII)

is reacted with methylamine, if appropriate in the presence of a diluent.

It is extremely surprising that, by the processes f) and g) according to the invention, 2-(2-hydroxyphenyl)-2-(methylimino)-N-methylacetamide of the formula (IV) is formed spontaneously even with aqueous methylamine solution and can be isolated as a stable product, since imines are frequently unstable compounds which in most cases can only be prepared with the aid of dehydrating agents, under dehydrating conditions or with the aid of catalysts (cf. S. Dayagi, Y. Degani in The Chemistry of the carbon-nitrogen bond, page 64, Intersc. Publ. (1970) in The chemistry of functional groups, S. Patai, editor).

The processes f) and g) according to the invention have a number of advantages. Thus, 2-(2-hydroxyphenyl)-2-(methylimino)-N-methylacetamide of the formula (IV) can be obtained in high yields and purities from easily obtainable starting materials, under conditions which do not cause any technical problems at all.

The formula (VII) provides a general definition of the alkyl (2-hydroxyphenyl)-oxoacetates required as starting materials for carrying out the process f) according to the invention. In this formula (VII), A represents alkyl or optionally substituted aryl, preferably methyl, ethyl, n- or i-propyl, n-, s- or i-butyl, n-pentyl, i-pentyl or substituted phenyl, where the substituents are preferably selected from the following list: fluorine, chlorine, bromine, methyl, ethyl, n- or i-propyl, n-, s-, i- or t-butyl.

The alkyl (2-hydroxyphenyl)-oxoacetates of the general formula (VII) are known and can be prepared by known methods (compare, for example. J. Chem. Soc., Chem. Commun. (1972), (11), 668).

The 2-(2-hydroxyphenyl)-2-N-methylacetamide of the formula (VI) required as starting material for carrying out the processes c) and e) according to the invention have hitherto not been disclosed and, as novel chemical compound, also forms part of the subject-matter of the present application.

2-(2-Hydroxyphenyl)-2-oxo-N-methylacetamide of the formula (VI)

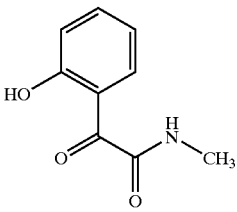

(VI)

is obtained when h) an alkyl (2-hydroxyphenyl)-oxoacetate of the general formula (VII)

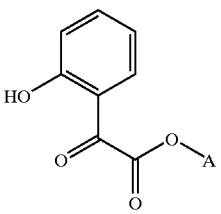

(VII)

in which
A represents alkyl or optionally substituted aryl,
is reacted with methylamine, if appropriate in the presence of a diluent, and following the reaction, the reaction mixture is treated with an acid, or when i) 1-benzofuran-2,3-dione of the formula (VIII)

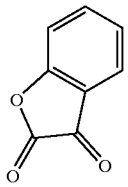

(VIII)

is reacted with methylamine, if appropriate in the presence of a diluent, and following the reaction, the reaction mixture is treated with an acid.

It is extremely surprising that, by the processes i) and h) according to the invention, 2-(2-hydroxyphenyl)-2-oxo-N-methylacetamide of the formula (VI) is obtained in good yields.

The processes h) and i) according to the invention have a number of advantages. Thus, 2-(2-hydroxyphenyl)-2-oxo-N-methylacetamide of the formula (VI) can be obtained in high yields and purities from easily obtainable starting materials, under conditions which do not cause any technical problems at all.

The alkyl (2-hydroxyphenyl)-oxoacetates of the general formula (VII) are known and can be prepared by known methods (compare, for example, J. Chem. Soc., Chem. Commun. (1972), (11), 668).

Suitable alkylating agents of the formula (III) furthermore required as starting materials for carrying out the process a) according to the invention are all chemical compounds which can transfer alkyl groups. Preference is given to chloromethane, bromomethane, iodomethane, dimethyl sulphate and dimethyl carbonate. Particular preference is given to dimethyl sulphate and chloromethane.

The alkoxyamines of the formula (V) and their acid addition complexes furthermore required as starting materials for carrying out the processes b) and c) according to the invention are chemicals for synthesis which are commercially available. Preferred acid addition complexes are the hydrochlorides, hydrogen sulphates or sulphates.

Hydroxylamine and its acid addition complexes which are furthermore required for carrying out the processes d) and e) according to the invention are chemicals for synthesis which are commercially available. Preferred acid addition complexes are the hydrochlorides, hydrogen sulphates or sulphates.

Methylamine which is furthermore required as starting material for carrying out the processes f), g), h) and i) according to the invention is a chemical for synthesis which is commercially available. It can be used both as gas and as alcoholic or aqueous solution.

The 1-benzofuran-2,3-dione furthermore required as starting material for carrying out the processes g) and i) according to the invention is known (cf. K. Fries, W. Pfaffendorf, Chem. Ber. 45, 156, (1912)) and can be prepared by known methods (compare, for example, W. Logemann et al., Chem. Ber. 96, 2248, (1963), G. A. Russell et al., J. Am. Chem. Soc. 92, 2762 (1970)).

Suitable diluents for carrying out the process a) according to the invention are all inert organic solvents. These include, by way of example and by way of preference, aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as, for example, acetone, butanone, methyl isobutyl ketone or cyclohexanone; nitrites, such as, for example, acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process a) according to the invention is, if appropriate, carried out in the presence of a suitable acid acceptor. Suitable acid acceptors are all customary inorganic or organic bases. These include, by way of example and by way of preference, alkaline earth metal or alkali metal hydroxides, alkoxides, acetates, carbonates or bicarbonates, such as, for example, sodium methoxide, sodium ethoxide, potassium tert-butoxide, sodium hydroxide, potassium hydroxide, sodium acetate, potassium acetate, sodium carbonate, potassium carbonate, potassium bicarbonate or sodium bicarbonate, and also tertiary amines, such as, for example, trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU). Preference is given to using potassium carbonate, sodium hydroxide or potassium hydroxide in process a).

The process a) according to the invention is, if appropriate, carried out in the presence of a suitable phase-transfer catalyst. Suitable phase-transfer catalysts are, by way of example and by way of preference, quaternary ammonium salts, such as, for example, tetrabutylammonium bromide, chloride, hydrogen sulphate or sulphate, methyltrioctylammonium bromide or chloride, hydrogen sulphate or sulphate or 4-dimethylamino-N-(2-ethylhexyl)-pyridinium bromide or chloride, hydrogen sulphate or sulphate, quaternary phosphonium salts, such as, for example, tributyl-tetradecylphosphonium bromide or chloride, tetraphenylphosphonium bromide or chloride, crown ethers, such as, for example, dibenzo-18-crown-6, guanidinium salts, such as, for example, hexaalkylguanidinium chloride, and also polyethylene glycol derivatives. Preference is given to using tetrabutylammonium bromide or tetrabutylammonium chloride in the process a) according to the invention.

When carrying out the process a) according to the invention, the reaction—temperatures can be varied within a relatively wide range. In general, the process is carried out at temperatures from −80° C. to 100° C., preferably at temperatures from 0° C. to 60° C.

In general, the process a) according to the invention is carried out under atmospheric pressure. However, it is also possible to operate under elevated or reduced pressure—in general between 0.1 bar and 10 bar.

For carrying out the process a) according to the invention for preparing the compounds of the formula (I), in general from 1 to 15 mol, preferably from 1 to 4 mol, of alkylating agent of the formula (III) are employed per mole of the 2-(2-hydroxyphenyl)-2-(hydroxyimino)-N-methylacetamide of the formula (II).

The process a) according to the invention is generally carried out as follows: The 2-(2-hydroxyphenyl)-2-(hydroxyimino)-N-methylacetamide of the formula (II) is, preferably in the presence of a diluent, admixed with a base and, if appropriate, a phase-transfer catalyst. The alkylating agent of the formula (III) is added and the mixture is stirred, if appropriate at elevated temperature, until the reaction has gone to completion. After the reaction has ended, the mixture is worked up in a customary manner. For example, volatile solvent components are distilled off and the mixture is admixed with water, resulting in the crystallization of the product.

Suitable diluents for carrying out the processes b), c), d) and e) according to the invention are all inert organic solvents. These include, by way of example and by way of preference, ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric—triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene—glycol monoethyl ether. Preferred diluents are alcohols, mixtures thereof with water or pure water.

The processes b), c), d) and e) according to the invention are, if appropriate, carried out in the presence of a buffer medium. Suitable buffer media are all customary acid/salt mixtures which buffer the pH in the range from 1 to 7. Preference is given to the mixture acetic acid/sodium acetate or no buffer medium.

When carrying out the processes b), c), d) and e) according to the invention, the reaction temperatures can be varied within a relatively wide range. In general, the processes are carried out at temperatures from −20° C. to 150° C., preferably at temperatures from 0° C. to 80° C.

The processes b), c), d) and e) according to the invention are generally carried out under atmospheric pressure. However, it is also possible to operate under elevated or reduced pressure—in general between 0.1 bar and 10 bar.

For carrying out the process b) according to the invention for preparing the compounds of the formula (I), in general from 1 to 15 mol, preferably from 1 to 4 mol, of alkoxyamine of the formula (V) or an acid addition complex thereof are employed per mole of the 2-(2-hydroxyphenyl)-2-(methylimino)-N-methylacetamide of the formula (IV).

For carrying out the process c) according to the invention for preparing the compounds of the formula (I), in general from 1 to 15 mol, preferably from 1 to 4 mol, of alkoxyamine of the formula (V) or an acid addition complex thereof are employed per mole of the 2-(2-hydroxyphenyl)-2-(oxo)-N-methylacetamide of the formula (VI).

For carrying out the process d) according to the invention for preparing the compounds of the formula (II), in general from 1 to 15 mol, preferably from 1 to 4 mol, of hydroxylamine or an acid addition complex thereof are employed per mole of the 2-(2-hydroxyphenyl)-2-(methylimino)-N-methylacetamide of the formula (IV).

For carrying out the process e) according to the invention for preparing the compounds of the formula (II), in general from 1 to 15 mol, preferably from 1 to 4 mol, of hydroxylamine or an acid addition complex thereof are employed per mole of the 2-(2-hydroxyphenyl)-2-oxo-N-methylacetamide of the formula (VI).

The processes b) and c) according to the invention are generally carried out as follows. The 2-(2-hydroxyphenyl)-2-(methylimino)-N-methylacetamide of the formula (IV) or the 2-(2-hydroxyphenyl)-2-(oxo)-N-methylacetamide of the formula (VI) is, preferably in the presence of a diluent, admixed with alkoxyamine or its acid addition complex and, if appropriate, the buffer medium, and heated. After the reaction has ended, the mixture is worked up in a customary manner. For example, volatile solvent components are distilled off and the mixture is admixed with water, resulting in the crystallization of the product.

The processes d) and e) according to the invention are generally carried out as follows. The 2-(2-hydroxyphenyl)-2-(methylimino)-N-methylacetamide of the formula (IV) or the 2-(2-hydroxyphenyl)-2-(oxo)-N-methylacetamide of the formula (VI) is, preferably in the presence of a diluent, admixed with hydroxylamine or its acid addition complex and, if appropriate, the buffer medium, and heated. After the reaction has ended, the mixture is worked up in a customary manner. For example, volatile solvent components are distilled off and the mixture is admixed with water, resulting in the crystallization of the product.

Suitable diluents for carrying out the processes f), g), h) and i) according to the invention are all inert organic solvents. These include, by way of example and by way of preference, alicyclic or aromatic hydrocarbons, such as, for example, cyclohexane, methylcyclohexane, benzene, toluene, xylene or decalin; halogenated hydrocarbons, such as, for example, chlorobenzene, dichlorobenzene, dichloromethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

When carrying out the processes f), g), h) and i) according to the invention, the reaction temperatures can be varied within a relatively wide range. In general, the processes are carried out at temperatures from −60° C. to 100° C., preferably at temperatures from 0° C. to 80° C.

The processes. f), g), h) and i) according to the invention are generally carried out under atmospheric pressure. However, it is also possible to operate under elevated or reduced pressure—in general between 0.1 bar and 10 bar.

In the processes h) and i) according to the invention, the acids used are mineral acids or carboxylic acids, in particular dilute mineral acids or acetic acid.

For carrying out the process f) according to the invention for preparing the compound of the general formula (IV), in general from 2 to 30 mol, preferably from 2 to 10 mol, of methylamine are employed per mole of the alkyl (2-hydroxyphenyl)-oxoacetate of the general formula (VII).

For carrying out the process g) according to the invention for preparing the compound of the formula (IV), in general from 2 to 30 mol, preferably from 2 to 10 mol, of methylamine are employed per mole of the 1-benzofuran-2,3-dione of the formula (VII).

For carrying out the process h) according to the invention for preparing 2-(2-hydroxyphenyl)-2-oxo-N-methylacetamide of the formula (VI), in general from 2 to 30 mol, preferably from 2 to 10 mol, of methylamine are employed per mole of the compounds of the formula (VII).

For carrying out the process i) according to the invention for preparing 2-(2-hydroxyphenyl)-2-oxo-N-methylacetamide of the formula (VI), in general from 2 to 30 mol, preferably from 2 to 10 mol, of methylamine are employed per mole of the 1-benzofuran-2,3-dione of the formula (VIII).

The processes f) and g) according to the invention are generally carried out as follows. The alkyl (2-hydroxyphenyl)-oxoacetate of the general formula (VII) or the 1-benzofuran-2,3-dione of the formula (VIII) is, preferably in the presence of a diluent, admixed with gaseous methylamine or an aqueous or alcoholic solution thereof. After the reaction has ended, the mixture is worked up in a customary manner. For example, volatile components are distilled off or the product is filtered off, giving the product in high purity.

The processes h) and i) according to the invention are generally carried out as follows. The alkyl (2-hydroxyphenyl)-oxoacetate of the general formula (VII) or the 1-benzofuran-2,3-dione of the formula (VIII) is, preferably in the presence of a diluent, admixed with gaseous methylamine or an aqueous or alcoholic solution thereof. After the reaction has ended, the reaction mixture is treated with acids and then worked up in a customary manner. For example, volatile components are distilled off, giving the product in high purity.

2-(2-Hydroxyphenyl)-2-(alkoxyimino)-N-methylacetamide derivatives of the formula (I) can be employed as intermediates for preparing fungicides (compare, for example, EP-A 398692).

The compounds of the formula (II) and the formulae (IV) and (VI) can be employed as intermediates, in particular for preparing fungicides.

The examples below serve to illustrate the invention. However, the invention is not limited to the examples.

PREPARATION EXAMPLES

Example 1

Process f)

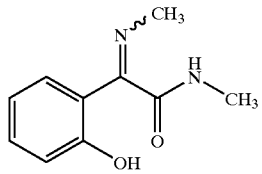

1 g of methyl 2-(2-hydroxyphenyl)-2-oxo-acetate (80% pure, 4.4 mmol) is dissolved in 10 ml of dioxane and admixed with 1.74 g of 30% strength aqueous methylamine solution (16.8 mmol), and the mixture is stirred at room temperature for 30 min. The mixture is evaporated to dryness under reduced pressure, admixed with acetonitrile and once more evaporated to dryness under reduced pressure. The crude product, obtained as an oil, is stirred with petroleum ether/diisopropyl ether (3:2), resulting in crystallization. The precipitate is filtered off with suction and dried under reduced pressure. This gives 0.65 g (77% of theory) of 2-(2-hydroxyphenyl)-N-methyl-2-(methylimino) acetamide.

NMR (D6-DMSO): δ=2.8 (d, 3H); 3.28 (s, 3H), 6.9 (m 2H), 7.2 (m, 1H), 7.35 (m, 1H), 8.9 (b, 1H), 14.2 (s, 1H) ppm.

Example 2

Process b)

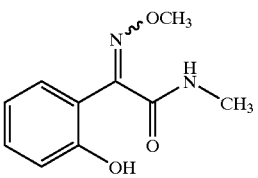

0.6 g of 2-(2-hydroxyphenyl)-N-methyl-2-(methylimino) acetamide (3.12 mmol) is dissolved in 12 ml of methanol and 3 ml of water, and the mixture is admixed with 0.52 g of methoxyamine hydrochloride (6.25 mmol) and stirred at room temperature for 18 hours. Under reduced pressure, the reaction solution is concentrated to give a solid residue which is stirred with ice-water, filtered off with suction and dried on clay. This gives 0.5 g (77% of theory) of 2-(2-hydroxyphenyl)-2-(methoxyimino)-N-methylacetamide.

Example 3

Process h)

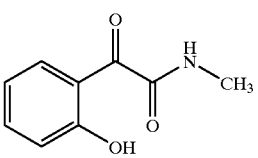

2.4 g of methyl 2-(2-hydroxyphenyl)-2-oxo-acetate (80% pure, 10.7 mmol) are dissolved in 25 ml of ethylene glycol dimethyl ether and admixed with 1.93 g of 30% strength aqueous methylamine solution (18.6 mmol), and the mixture is stirred at room temperature for 30 min. The mixture is admixed with 20 ml of saturated NaCl solution and extracted three times with in each case 25 ml of ethyl acetate. The combined organic phases are extracted by stirring with 50 ml of 10% strength aqueous hydrochloric acid for 15 min. The organic phase is dried and concentrated under reduced pressure to give an oil (2.45 g).

Column chromatography (silica gel/$CH_2Cl_2$) gives 1.3 g (76% of theory) of 2-(2-hydroxyphenyl)-2-(oxo)-N-methylacetamide.

NMR (D6-DMSO): δ=2.77 (d, 3H); 6.97 (m, 2H); 7.55 (m, 1H); 7.71 (m, 1H); 8.8 (b, 1H); 11.1 (s, 1H) ppm.

What is claimed is:

1. A process for preparing a compound of the formula (I)

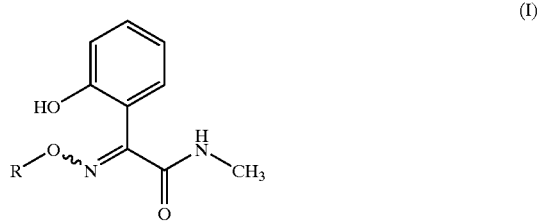

wherein

R represents substituted or unsubstituted alkyl, the process comprising:

(a) reacting a compound of the formula (II)

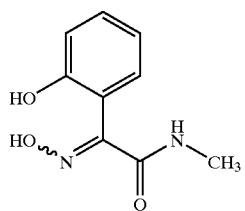

with an alkylating agent of the formula (III)

R—X  (III)

wherein
R is as defined above, and
X represents halogen, —O—CO—O—R, —O—SO$_2$—R$^1$ or —O—SO$_2$—O—R, wherein R is as defined above and R$^1$ represents alkyl or optionally alkyl-substituted phenyl, if appropriate in the presence of a diluent and if appropriate in the presence of an acid acceptor, if appropriate in the presence of a phase-transfer catalyst, or (b) reacting a compound of the formula (IV)

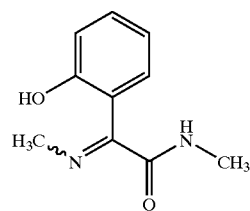

with an alkoxyamine of the formula (V)

R—O—NH$_2$  (V)

wherein
R is as defined above,
or an acid addition complex thereof,
if appropriate in the presence of a diluent and if appropriate in the presence of a buffer medium

* * * * *